United States Patent
Tai et al.

(10) Patent No.: US 7,022,882 B2
(45) Date of Patent: Apr. 4, 2006

(54) NMDA RECEPTOR CHANNEL BLOCKER WITH NEUROPROTECTIVE ACTIVITY

(75) Inventors: Kwok-Keung Tai, Santa Ana, CA (US); Sylvie E. Blondelle, San Diego, CA (US); Richard A. Houghten, Solana Beach, CA (US); Mauricio Montal, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/381,956

(22) PCT Filed: Oct. 5, 2001

(86) PCT No.: PCT/US01/42521

§ 371 (c)(1),
(2), (4) Date: Sep. 25, 2003

(87) PCT Pub. No.: WO02/28814

PCT Pub. Date: Apr. 11, 2002

(65) Prior Publication Data

US 2004/0054013 A1    Mar. 18, 2004

Related U.S. Application Data

(60) Provisional application No. 60/238,739, filed on Oct. 6, 2000.

(51) Int. Cl.
*C07C 211/13* (2006.01)
*C07C 211/27* (2006.01)
*C07C 215/52* (2006.01)
*A61K 31/135* (2006.01)

(52) U.S. Cl. ............ 564/372; 564/355; 564/360; 564/367; 564/370; 514/653; 514/654; 514/655

(58) Field of Classification Search ............ 564/355, 564/360, 367, 370, 372; 514/653–655
See application file for complete search history.

(56) References Cited

U.S. PATENT DOCUMENTS

| | | | |
|---|---|---|---|
| 5,242,947 A | 9/1993 | Cherksey et al. | |
| 5,432,202 A | 7/1995 | Cherksey et al. | |
| 5,539,120 A | 7/1996 | Griffith et al. | |
| 5,641,861 A * | 6/1997 | Dooley et al. | 530/329 |
| 5,919,897 A * | 7/1999 | Dooley et al. | 530/330 |

FOREIGN PATENT DOCUMENTS

WO    WO 96 40208    12/1996

OTHER PUBLICATIONS

Database CAPLUS on STN, Acc. No. 1997:425990, Dooley et al., US 5,641,861 (Jun. 24, 1997) (abstract).*
Database CAPLUS on STN, Acc. No. 1999:426832, Dooley et al., US, 5,919,897 (Jul. 6, 1999) (abstact).*
Database CAPLUS on STN, Acc. No. 1997:140254, Dooley et al. WO 96/40208 (Dec. 19, 1996) (abstract).*
Carter, Many agents that antagonize the NMDA receptor-channel complex in Vivo also cause disturbances of motor coordination. J. Pharmacol. Exp. Ther., 269:: 573-580, 1994.
Dingledine et al., "Amino acid receptors and uptake systems in the mammalian central nervous system," Crit. Rev. Neurobiol., 4(1): 1-96, 1988.
Dorner et al., "The sysnthesis of peptidomimetic combinatorial libraries through successive amide alkylations." Bioorg. Medicinal Chem., 4:409-715, 1996.
Ferrer-Montiel et al., "Structural determinants of the blocker binding site in glutamate and NMDA receptors channels." Neuropharmacology, 37(2): 139-47, 1998.
Ferrer-Montiel et al., "Selected peptides targeted to the NMDA receptors channel protect neurons from excitotoxic death." Nat. Biotechnol., 16(3): 286-91, 1998.
Houghten, R.A., "General method for the rapid solid-phase synthesis of large numbers of peptides: Specificity of antigen-antibody interaction at the level of individual amino acids." Proc. Nat. Acad. Sci. USA, 82: 5131-5135, 1985.
Houghton et al., "Generation and use of synthetic peptide combinatorial libraries for basic research and drug discovery." Nature, 354: 84-86, 1991.

(Continued)

*Primary Examiner*—Brian Davis
(74) *Attorney, Agent, or Firm*—Stacy L. Taylor; Foley & Lardner LLP (57) ABSTRACT

Neuroprotectant agents are provided which do not contain peptides and axe protected from the degradation that limits the use of peptide-based drugs in systemic circulation. With great selectivity for NMDA receptors, the agents exert an open channel block on NMDA receptors, and protect neuronal cells containing such receptors from excitotoxic cell death.

6 Claims, 11 Drawing Sheets

OTHER PUBLICATIONS

LeBourdelles et al., "Cloning, functional coexpression, and pharmacological characterization of human cDNAs encoding NMDA receptors NR1 and NR2A subunits," J.Neurochem., 62(6): 2091-8, 1994.

Muir and Lees, "Clinical experience with excitatory amino acid antagonist drugs." Stroke, 26(3): 503-13, 1995.

Nefzi et al., "Parallel solid phase synthesis of tetrasubstituted diethylenetriamines via selective amide alkylation and exhaustive reduction of N-acylated dipeptides." Tetrahedron, 55: 335-344, 1999.

Ostresh et al., "The solid phase synthesis of tri-substituted bicyclic guanidines via cyclization of reduced N-acylated dipeptides." J.Org. Chem., 63:8622-8623, 1998.

Planells-Cases et al., "Molecular cloning, functional expression, and pharmacological characterization of an N-methyl-D-aspartate receptors subunit from human brain." Proc. Nat. Acad. Sci. USA, 90(11): 5057-61, 1993.

Rothman and Olney, "Excitotoxicity and the NMDA receptor—still lethal after eight years." Trends Neurosci., 18(2): 57-58, 1995.

Schinder et al., "Mitochondrial dysfunction is a primary event in glutamate neurotoxicity." J.Neurosci., 16(19): 6125-33, 1996.

Sun et al., "Molecular cloning, chromosomal mapping and functional expression of human brain glutamate receptors." Proc. Natl. Acad. Sci. USA, 89: 1443-1447, 1992.

Woodhull, A.M., "Ionic blockade of sodium channels in nerve." J.Gen.Physiol., 61:687-708, 1973.

Zarei and Dani, "Ionic permeability characteristics of the N-methyl-D-aspartate receptor channel." J.Gen.Physiol., 1103(2): 231-48, 1994.

International Search Report for International Application No. PCT/US01/42521.

* cited by examiner

FIG. 1A

SUBLIBRARY 1

SUBLIBRARY 2

FIG. 1B

FIG. 2A  $O^2$ = methyl

FIG. 2B  $O^2$ = ethyl

FIG. 2C  $O^2$ = benzyl

FIG. 2D  $O^2$ = naphthylmethyl

FIG. 2E  $O^4$ = methyl

FIG. 2F  $O^2$ = ethyl

FIG. 2G  $O^4$ = benzyl

FIG. 2H  $O^4$ = naphthylmethyl

FIG. 3A

| COMPOUND NUMBER | R1 | R2 | R3 | R4 |
|---|---|---|---|---|
| 1 | S-4-hydroxybenzyl | benzyl | N-methyl,N-benzylaminobutyl | benzyl |
| 2 | S-4-hydroxybenzyl | benzyl | S-4-hydroxybenzyl | methyl |
| 3 | S-4-hydroxybenzyl | benzyl | S-4-hydroxybenzyl | benzyl |
| 4 | S-4-hydroxybenzyl | benzyl | R-2-naphthylmethyl | methyl |
| 5 | S-4-hydroxybenzyl | benzyl | S-isopropyl | benzyl |
| 6 | S-4-hydroxybenzyl | benzyl | R-isobutyl | naphthylmetl |
| 7 | S-4-hydroxybenzyl | benzyl | R-2-butyl | ethyl |
| 8 | S-2-butyl | benzyl | N-methyl, N-benzylaminobutyl | benzyl |
| 9 | S-2-butyl | benzyl | S-4-hydroxybenzyl | methyl |
| 10 | S-2-butyl | benzyl | S-4-hydroxybenzyl | benzyl |
| 11 | S-2-butyl | benzyl | R-2-naphthylmethl | methyl |
| 12 | S-2-butyl | benzyl | S-isopropyl | benzyl |
| 13 | S-2-butyl | benzyl | R-isobutyl | naphthylmetl |
| 14 | S-2-butyl | benzyl | R-2-butyl | ethyl |

NMDA RECEPTOR CHANNEL BLOCKER WITH NEUROPROTECTIVE ACTIVITY

This application claims the benefit of 60/238,739 filed on Oct. 6, 2000.

This application is a 317 of PCT/US01/42521 filed Oct. 5, 2001

FIELD OF THE INVENTION

The invention relates to neuroprotectants. In particular, the invention relates to a peptide-free N-methyl-D aspartate (NMDA) receptor open channel blocker, which mitigates excitotoxicity to aid in preventing neuronal cell death.

BACKGROUND OF THE INVENTION

NMDA receptor activity produces synaptic plasticity in the central nervous system that affects processes for learning and memory, including long-term potentiation and long-term depression (Dingledine R., Crit. Rev. Neurobiol., 4(1): 1–96, 1988). However, prolonged activation of NMDA receptor under pathological conditions (such as cerebral ischaemia and traumatic injury) causes neuronal cell death (Rothman S. M. and Olney J. W., Trends Neurosci., 18(2): 57–8, 1995). NMDA receptor-mediated excitotoxicity may contribute to the etiology or progression of several neurodegenerative diseases, such as Parkinson's disease and Alzheimer's disease. Since open channel blockers of NMDA receptors were shown, in the late 1980s, to have potential for therapy of ischemic stroke, the receptor has been considered an attractive therapeutic target for the development of neuroprotective agents. Unfortunately, the development of these compounds as neuroprotectants is often limited by their psychiatric side-effects associated with their undesired pharmacodynamic properties such as slow dissociation from the receptor (Muir K. W. and Lees K. R., Stroke, 26(3):503–13, 1995).

The advent of combinatorial chemistry technology in recent years has greatly facilitated the process of drug discovery. For example, a set of arginine-rich hexapeptides, which potently blocked NMDA receptor, have recently been identified from a peptide combinatorial library (Ferrer-Montiel A. V., et al., Nat. Biotechnol., 16(3):286–91, 1998). However, development of peptides as drugs is often hampered by their lack of oral bioavailability due to enzymatic degradation before entry into systemic circulation.

SUMMARY OF THE INVENTION

The invention provides open-channel blockers for NMDA receptor which do not contain peptides. As such, the compounds are protected from the degradation that limits the use of peptide-based drugs in systemic circulation. The compounds are of the formula:

The most potent of the inventive compounds is NBTA:

The inventive compounds protect neurons from NMDA neurotoxicity, without affecting other receptors, including glutamate receptors not of the NMDA subtype. It protects neurons in cultured hippocampal neurons from NMDA receptor-mediated excitotoxic cell death, and exerts non-competitive NMDA receptor blockade which is use- and strongly voltage-dependent, exhibiting fast offset kinetics.

Compounds with such fast offset kinetics and strong voltage-dependence often offer better therapeutic profile with fewer adverse-effects. The strong voltage-dependence of block enhances the ability of this compound to differentiate between transient physiological from sustained pathological activation of NMDA receptor because it allows the compound to leave the NMDA receptor channel rapidly upon normal transient activation by high concentration of glutamate at the synapse but to block the sustained activation by low concentrations of glutamate under certain pathological conditions. Recovery from the blocked state can be prompt and complete, allowing the channel block to be effective only during a brain insult, but not during normal synaptic activity.

These characteristics endow NBTA with properties of significant therapeutic potential. Thus, NBTA and its related compounds are efficacious, selective agents for highly targeted neuroprotection.

DESCRIPTION OF THE DRAWINGS

FIG. 1. Mixtures of dipeptidomimetic combinatorial library blocks recombinant NMDA receptor expressed in Xeniopus laevis oocytes. (A) Representation of the N-alkylated triamine positional screening-synthetic combinatorial library (PS-SCL). O represents a defined functionality derived from a single building block; X represents a mixture of functionalities derived from a mixture of all the building block used to generate the relevant diversity position. (B) A representative trace showing the glutamate and glycine-activated inward current through NMDA receptor is reversed by 10 μM of one mixture library with L-isoleucine and benzyl defined at position 1 and 2, respectively.

FIG. 3. The blocking activities of a series of 21 compounds were tested, the compounds having been synthesized based on the blocking profile of the library from the primary screening, and the results for 14 of the compounds are shown. (A) The amino acids and alkyl groups defined at each of the four positions of these compounds. Abbreviations: Bz: benzyl; Et: ethyl; ile: D-isoleucine; Ile: L-isoleucine; leu: leucine; lys(Boc): ε-t-butyloxycarbonyl-D-lysine; Me: methyl; nal: D-naphthylalanine; Tyr(2BrZ): 2-bromobenzy-loxycarbonl-L-tryosine; Tyr(tBu): t-butyl-L-tyrosine; Val: L-valine. (B) The blocking activities of these compounds were performed as described in Method. Values are expressed as mean±s.e. of 3–6 oocytes.

FIG. 4. Structure and LC-MS of NTA. Total ion counting is shown in (A), the UV absorbance in (B), the mass spectra and structure in (C). The mass spectral analysis was performed using a Finnigan Mat LCQ interfaced with a Waters analytical HPLC and a short Keystone $C_{18}$ column (3 μm, 4.6 mm×50 mm).

FIG. 5. The blocking action of NBTA is specific. 1 μM NBTA blocks NMDA receptors (A) but not non-NMDA glutamate receptor GluR1 (B). (C) Concentration-inhibition curves for antagonism of NMDA and GluR1 channels by NBTA, memantine, MK-801, and PCP. Data are fitted with the Hill equation. (D) Blocking activity of NBTA on wild-type NMDA receptors (NR1/NR2A (□))-$IC_{50}$=80+/−10 nM (n=6), $n_H$=0.8; and of indicated mutants, data for the latter as shown in the Figure.

FIG. 6. NBTA is an open-channel blocker of NMDA receptor. (A, B) The NBTA does not affect the $IC_{50}$ of L-glutamic acid or glycine for the NMDA receptors. Dose-response curves of L-glutamic acid (plus 20 μM glycine) or glycine (plus 200 μM L-glutamic acid) were obtained by activation of NMDA receptors in the absence (□) or presence (Δ) of 0.2 μM NBTA, n=4 oocytes. (C) NMDA current blockade by NBTA is voltage-dependent, as illustrated by currents evoked by 200 μM L-glutamic acid (plus 20 μM glycine) during a voltage-ramp protocol performed when currents reached a steady state. (D) Use dependence of NMDA receptor block by NBTA, at −80 mV. Pulse duration is indicated by the horizontal bar. Two pulses of 200 μM L-glutamic acid (plus 20 μM glycine) were first delivered as control, and then followed by a co-application the agonist with 0.1 μM NBTA. The NBTA induces a progressive block of the NMDA-receptor mediated currents. A complete recovery is observed at the second pulse of 200 μM L-glutamic and 20 μM glycine following the washout of NBTA.

DETAILED DESCRIPTION OF THE INVENTION

A. NBTA and Related NMDA Open Channel Blockers

1. Identification.

Figure 1A:
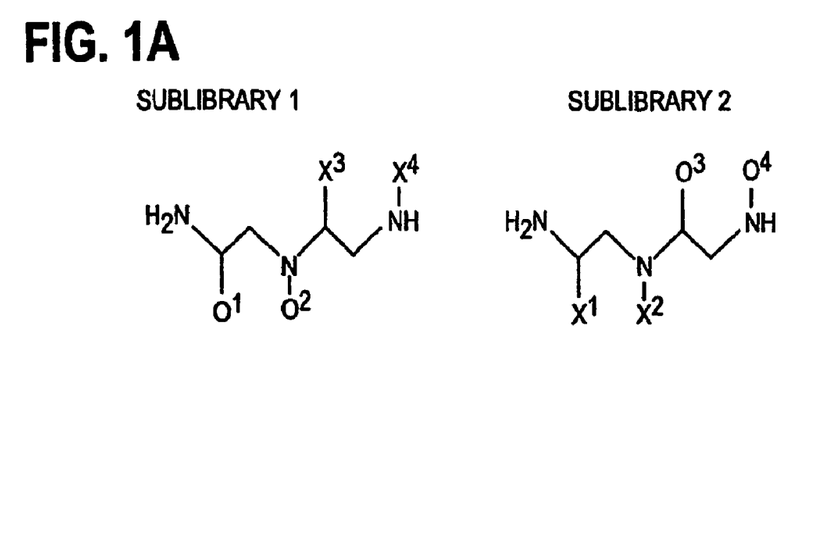

To identify NMDA receptor channel blockers, a N-alkylated triamine SCL generated in a dual defined positional scanning (PS) format was screened for block on recombinant NMDA receptors expressed in *Xenopus* oocytes. The PS-SCL consists of two sublibraries, as shown in FIG. 1A. Each sublibrary has two positions defined with a given amino acid ($O^1$ or $O^3$ for sublibrary 1 or 2) or a given alkyl group ($O^2$ or $O^4$ for sublibrary 1 or 2). The remaining two diversity positions were close to equimolar mixtures of amino acids or alkyl groups (X positions). Sublibrary 1 consists of 184 mixtures, while sublibrary 2 consists of 180 mixtures. Each mixture contains 230 compounds, for a total of 42,320 individual compounds in the entire library.

Figure 1B:
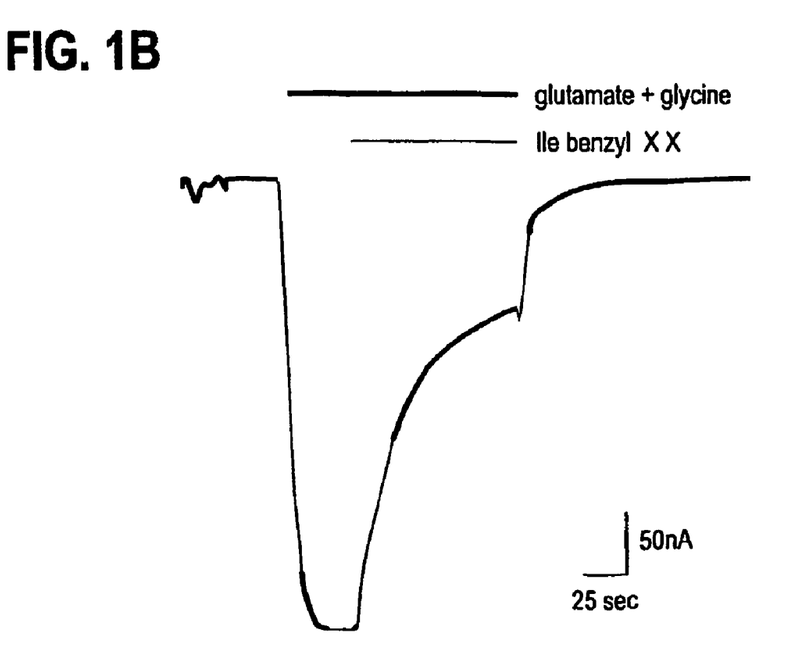
Figure 2A:
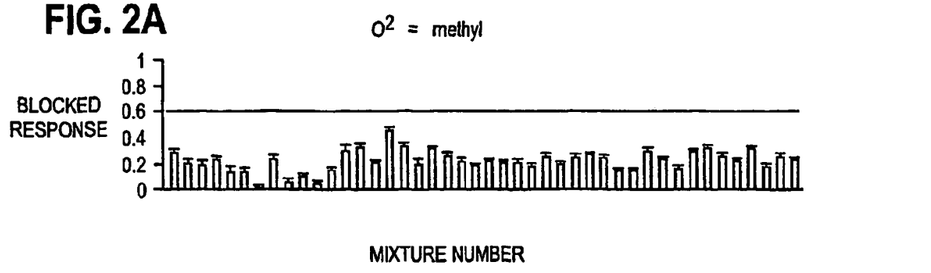
FIG. 2. The blocking profile of each of the mixture comprising the dipeptidomimetic combinatorial library on recombinant NMDA receptor expressed in Xenopus laevis oocytes. Each bar represents the blocked response by each of the 364 dipeptidomimetic mixtures at 10 μM. Values are given as mean±s.e. of 3–6 oocytes.
Figure 2B:
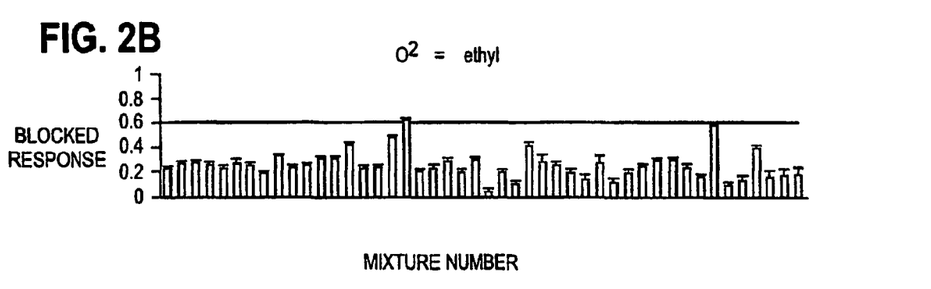
Figure 2C:
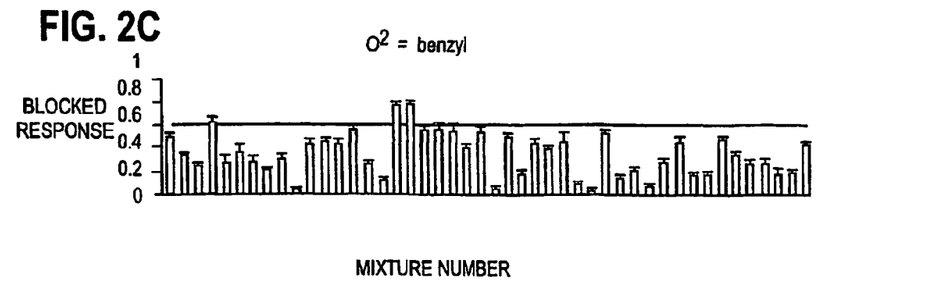
Figure 2D:
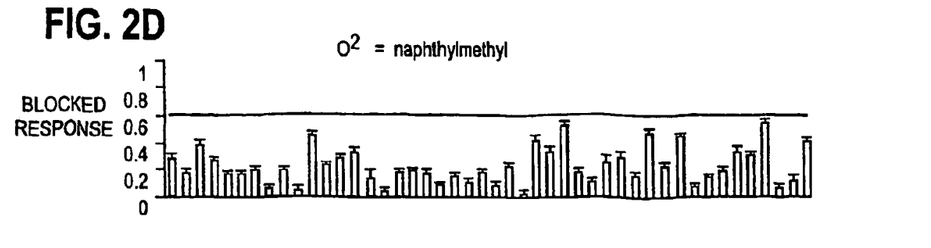
Figure 2E:
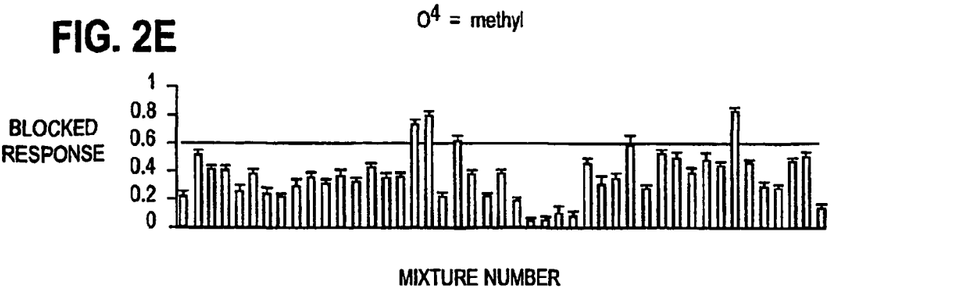
Figure 2F:
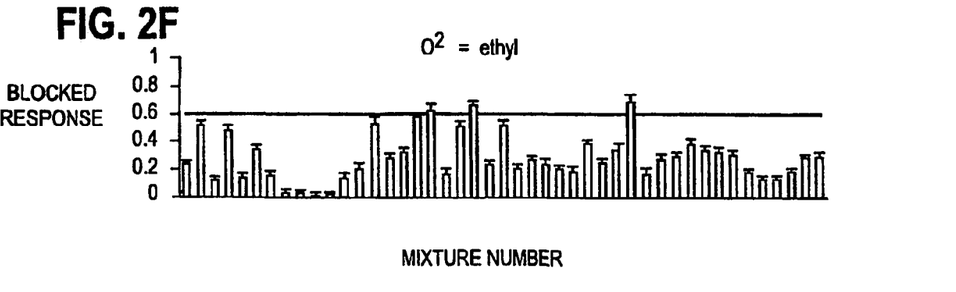
Figure 2G:
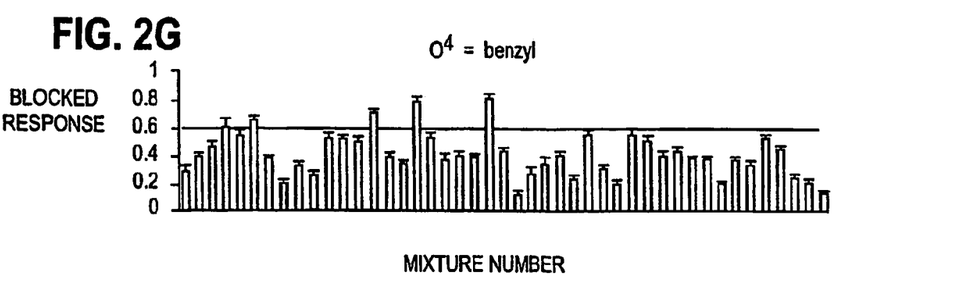
Figure 2H:
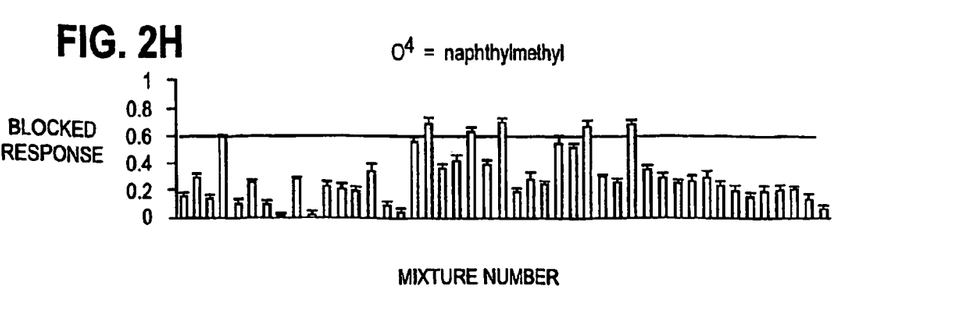

FIG. 1B shows the effect of a representative active mixture: coperfusion of the actile Ile(benzyl)XX library mixture at 10 μM with the agonist drastically diminishes the invoked current by 70%. Mixtures with $O^4$ defined with a methyl were among the most active compounds (blocked responses between 70 and 80%), while none of the mixtures having a methyl at $O^2$ showed a blocked response greater than 50%. All of the mixtures from sublibrary 1 showing responses greater than 60% were defined with a benzyl group at positions $O^2$, while other alkyl groups defined the active mixtures from sublibrary 2. These results indicate that not only the nature of the amino acid and the alkyl group are important for activity, but also their location within the molecule. Based on these screening results, 21 compounds were synthesized, based on the formula:

wherein the R substituents varied as follows: $R_1$ is a S-4-hydroxylbenzyl or a S-2-butyl; $R_2$ is a benzyl; $R_3$ is selected from the group consisting of N-methyl, N-benzylaminobutyl, S-4-hydroxybenzyl; R-2-naphthylmethyl, S-isopropyl, R-isobutyl and R-2-butyl; and $R_4$ is selected from the group consisting of benzyl, methyl, naphthylmethyl and ethyl.

Figure 3A:
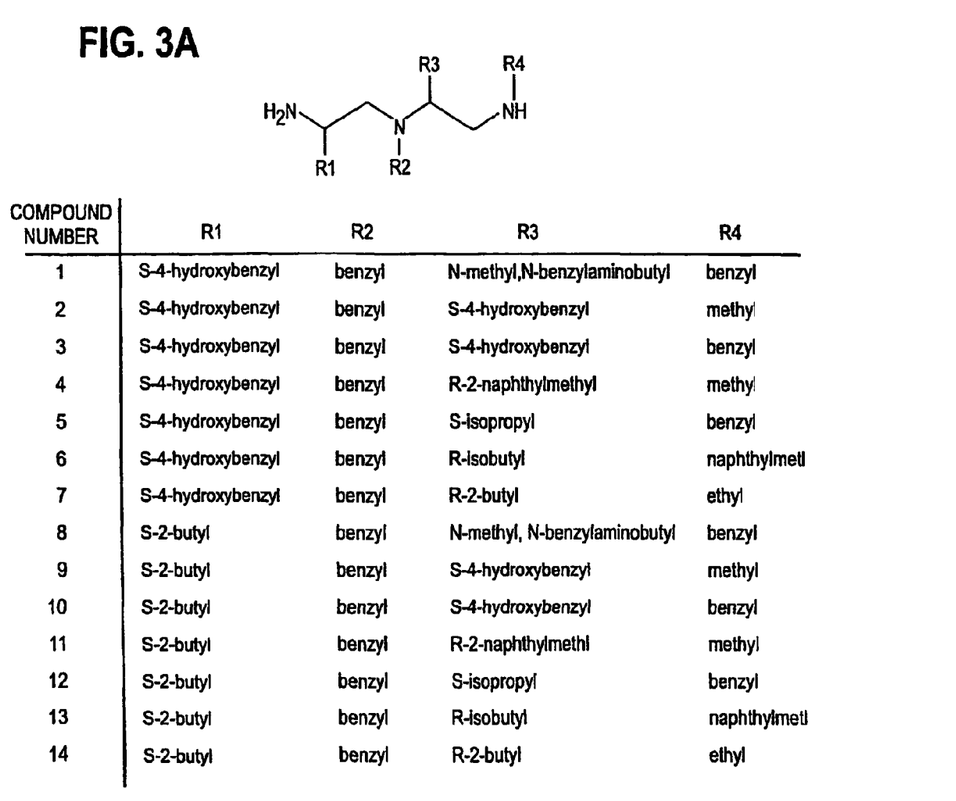
Figure 3B:
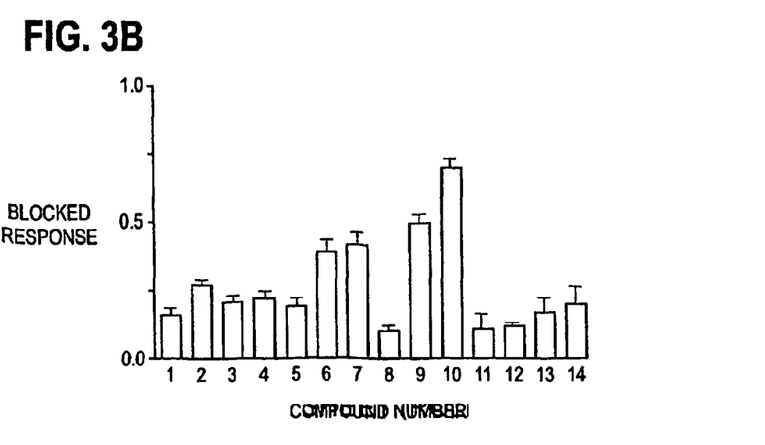
Figure 4A:
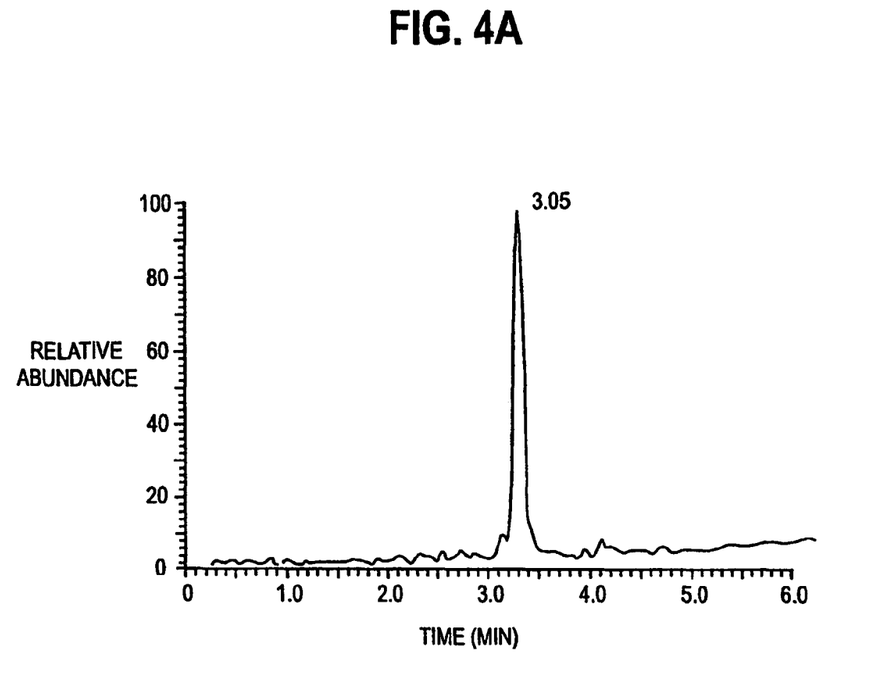
Figure 4B:
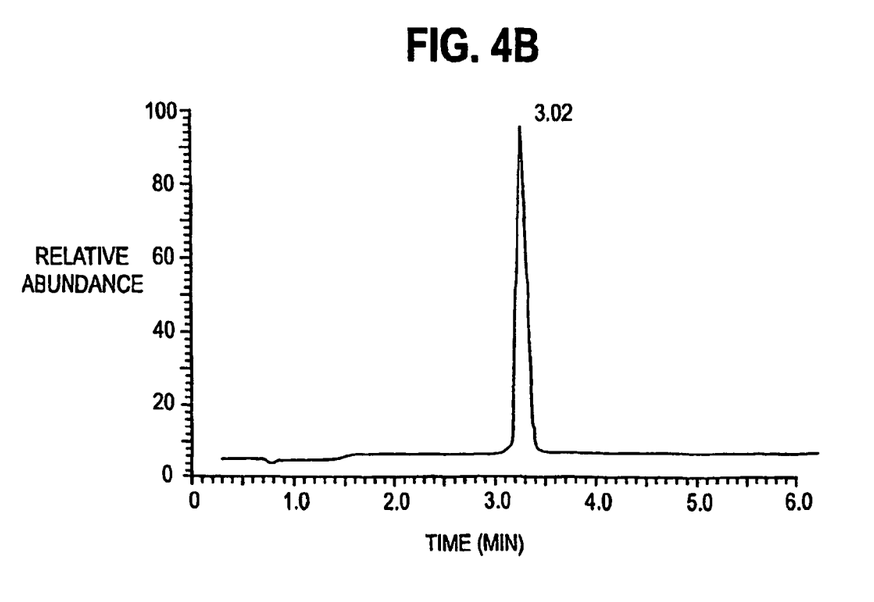
Figure 4C:
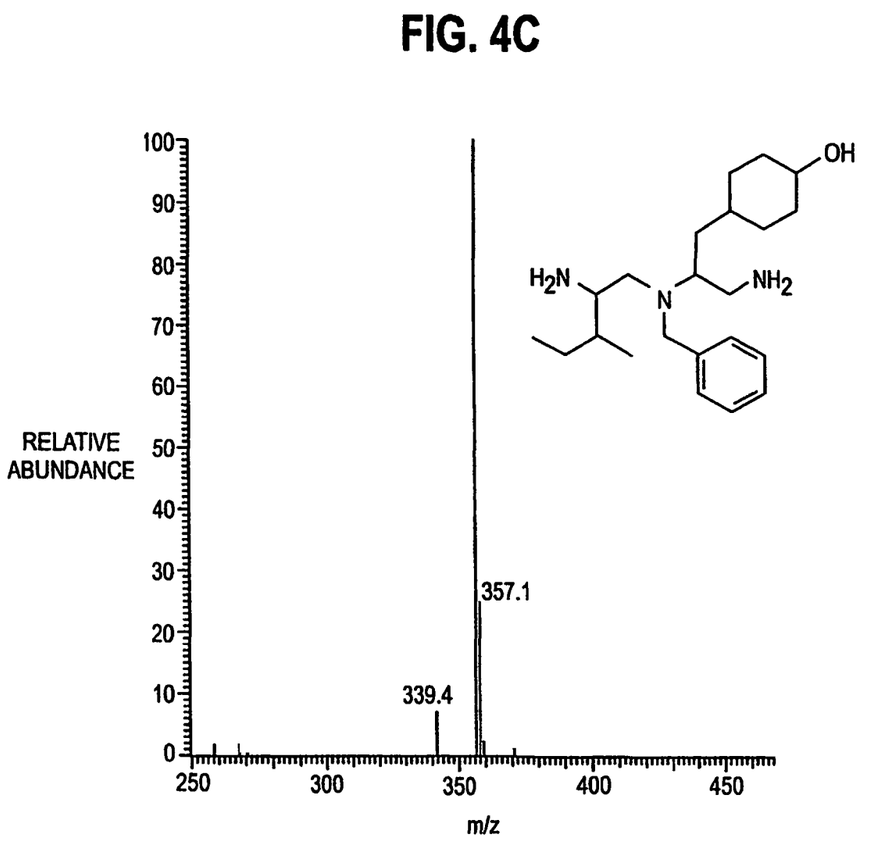

Compound #10 (NBTA) is the most potent N-benzylated triamine derivative of the 21 compounds tested, exerting 70±3% of NMDA current at 1 μM (FIG. 3B). The structural and analysis spectra of NBTA are shown in FIG. 4. NBTA has an S-2-butyl at $R_1$, a benzyl at $R_2$, a S-4-hydroxybenzyl at $R_3$, and a benzyl at $R_4$, as follows:

2. NBTA Activity.

Figure 5A:
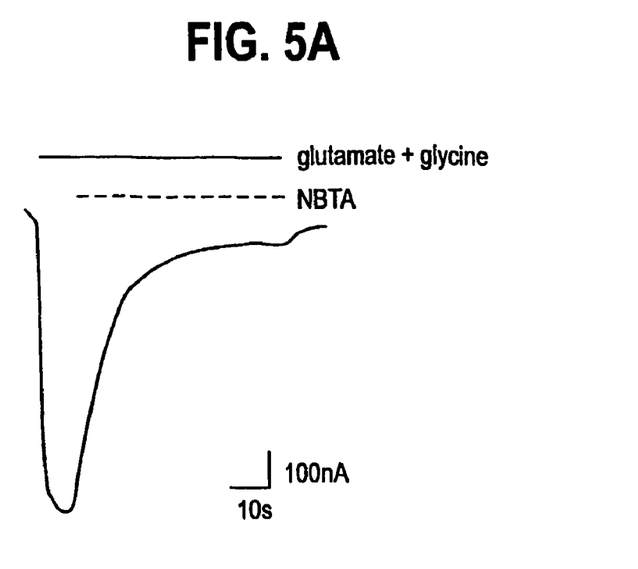
Figure 5B:
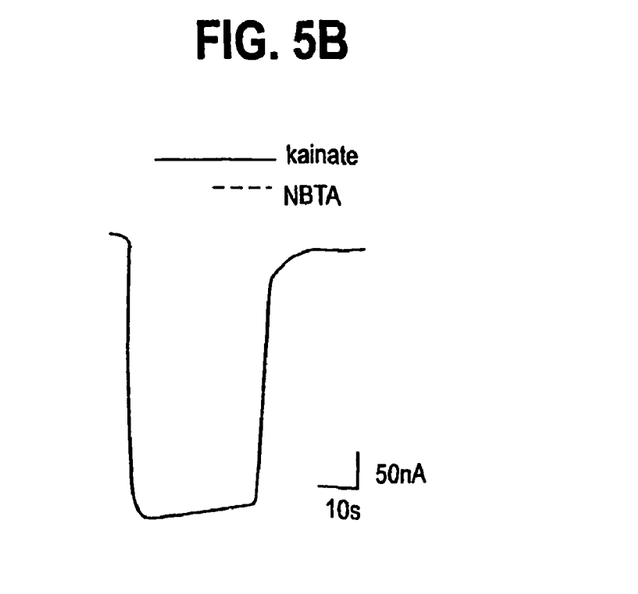

The blocking action of NBTA is specific, and is representative of all of the inventive compounds, although it possesses greater potency than its 20 relatives described in FIG. 3A. 1 μM NBTA blocks ~95% NMDA current but had no effect on the non-NMDA receptor glutamate receptor (GluR1), even at 1 mM (FIGS. 5B and C). Concentration-inhibition data fitted with a Hill equation yielded a mean $IC_{50}$ of 80±10 mM and a Hill coefficient close to unity (about 0.8) suggesting that NBTA binds to a single site (FIG. 5C).

Figure 5C:
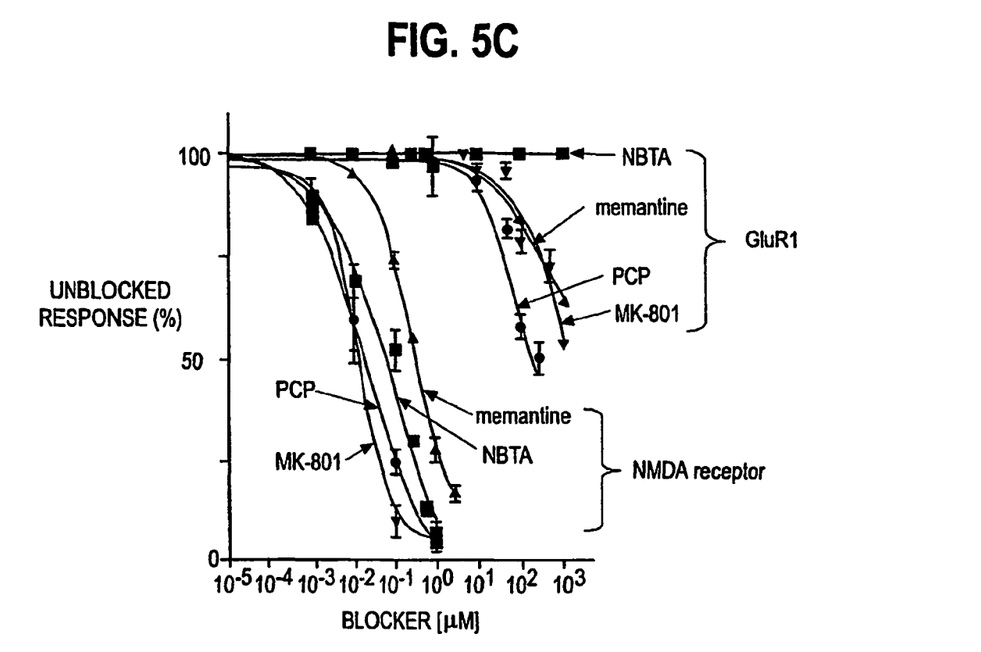

The remarkable selectively of NBTA for NMDA receptors is underscored by the data shown in FIG. 5C. Phencyclidine (PCP), sizolcipine (MK-801) and memantine (1-amino-3,5-dimethyladamantane) are high affinity, open channel blockers of the NMDA receptor. By contrast, non-NMDA receptors are only weakly responsive to these compounds. For example, they display 1,000 to 10,000 higher affinity for NMDA receptors than for AMPA receptors (FIG. 5C).

NBTA sharply discriminates between these two types of receptors, displaying high blocking potency for NMDA receptors, but no effect at all on AMPA receptors, even in the mM concentration range. This combination of potency and selectivity make NBTA a uniquely efficacious neuroprotectant.

B. Mechanism of Action of NBTA

Figure 6A:
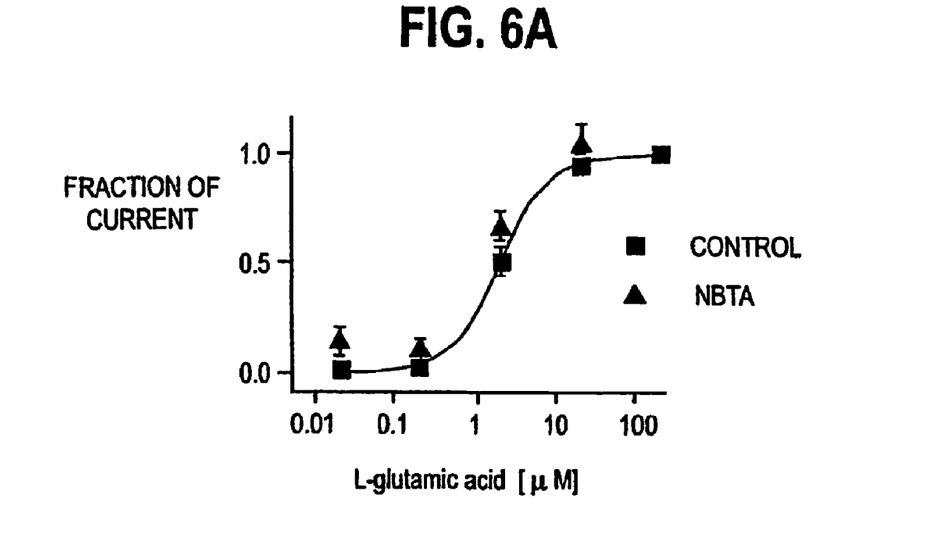
Figure 6B:
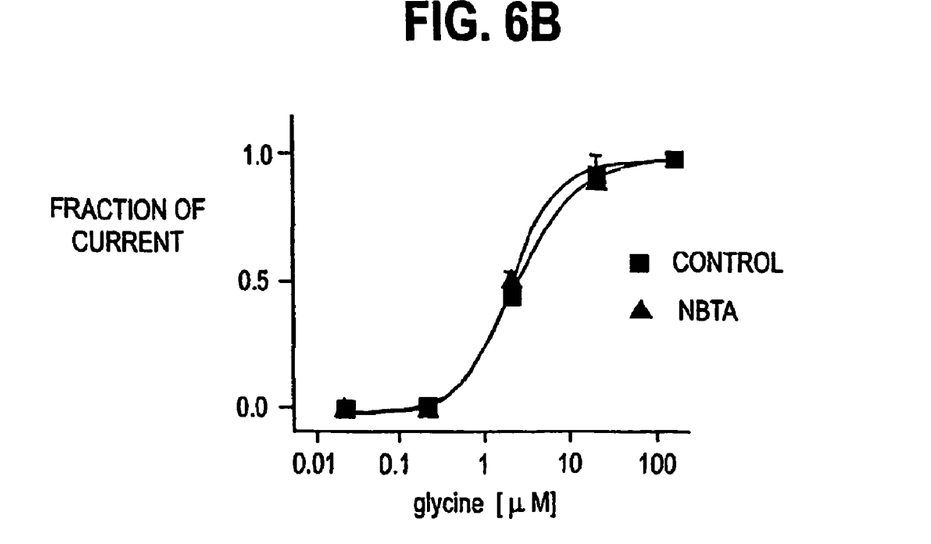
Figure 6C:
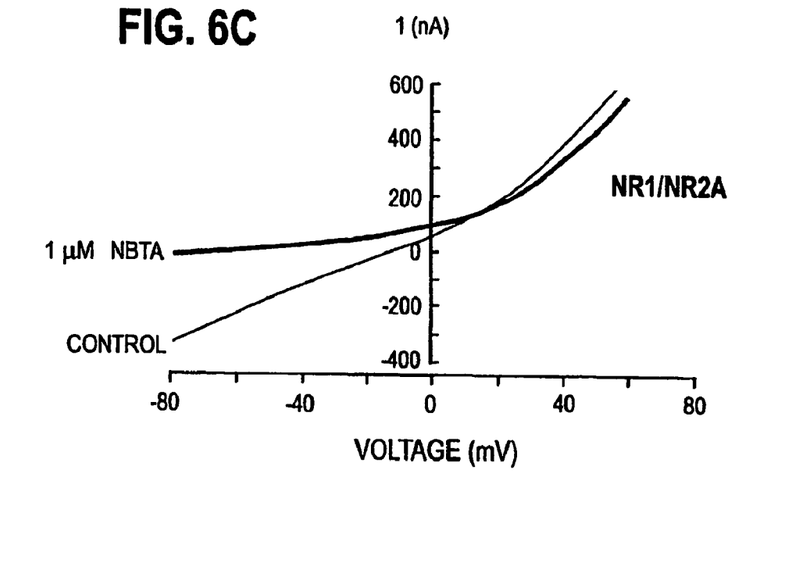

NMDA receptor mediated inward current can be attenuated by a number of mechanisms, depending on the site of action of the ligand at the receptor protein. NMDA receptor activity can be reduced by acting at various sites of the channel proteins, for instances, competitive antagonism at the glycine or glutamate binding sites, or allosteric modulating the proton and polyamines sites. The concentration-response curves L-glutamic acid (with glycine at 20 µM) dose-response curves performed in the absence or presence of 0.2 µM NBTA were similar (gives a mean $EC_{50}$ of 2.08±0.2 µM and 1.91±0.3 µM, respectively (FIG. 6A)). The $EC_{50}$ of glycine determined in the absence and presence of 0.2 µM compound were 2.22±0.21 µM (n=4) and 1.95±0.18 µM (n=4), respectively (FIG. 6B). The results suggest that NBTA is a non-competitive antagonist of NMDA receptor.

NBTA is an open-channel blocker for NMDA receptor. One of the key features of open-channel block is voltage-dependence. In general, open channel blockade exhibits marked voltage-dependent inhibition, that is, in the presence of a fixed concentration of blocker, the fraction of inhibited NMDA-evoked current increased with more negative membrane holding potentials. The active NBTA reduced more NMDA current at more hyperpolarized membrane potential, indicating that current reduction by NBTA is voltage-dependent (FIG. 5C, being more pronounced at more negative membrane potential than at positive membrane potential. A δ of 0.56 suggests that the compound transverses ~56% of the transmembrane electric field to reach its binding site(s) and this site is probably located in the pore. The observed current reduction presumably reflects occlusion of the channel pore.

Figure 6D:
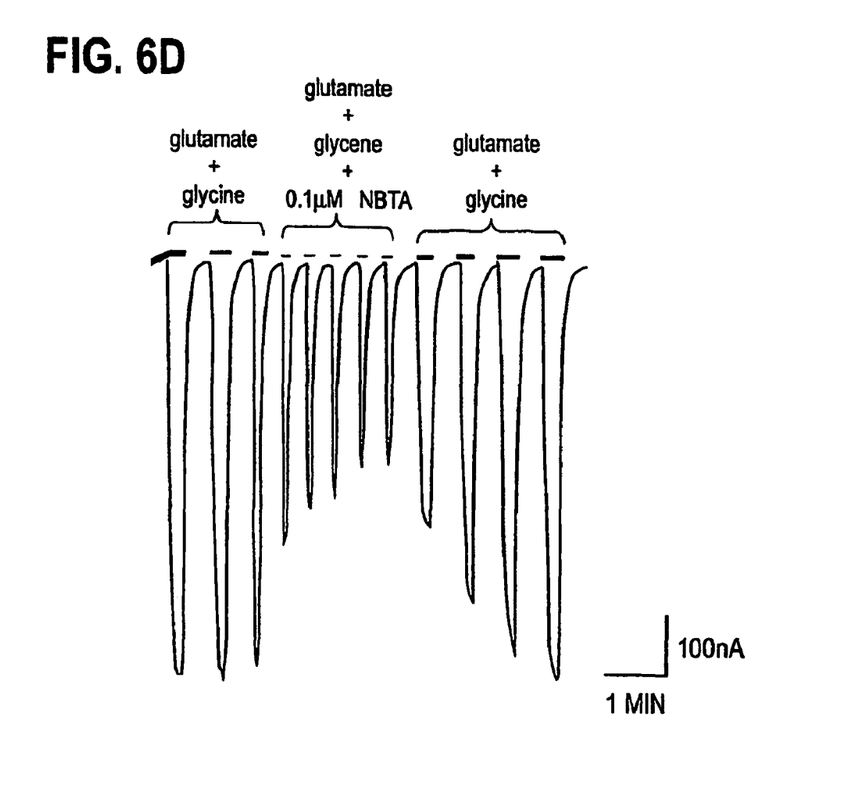

Another feature of open channel block is the use-dependence, at a fixed concentration of the open channel blocker, the fraction of current blockade increases with repetitive activation of the receptors. 0.1 µM NBTA induces a progressive blockade of the currents elicited by repetitive pulses of glutamate (200 µM) and glycine (20 µM) (FIG. 5E). A full recovery of responses was observed in the subsequent receptor activation following the washout of the compound (FIG. 6D). These results demonstrate that NBTA acts as an open-channel blocker at recombinant NMDA receptor.

C. Site of Action of NBTA on NMDA Receptors

Figure 5D:
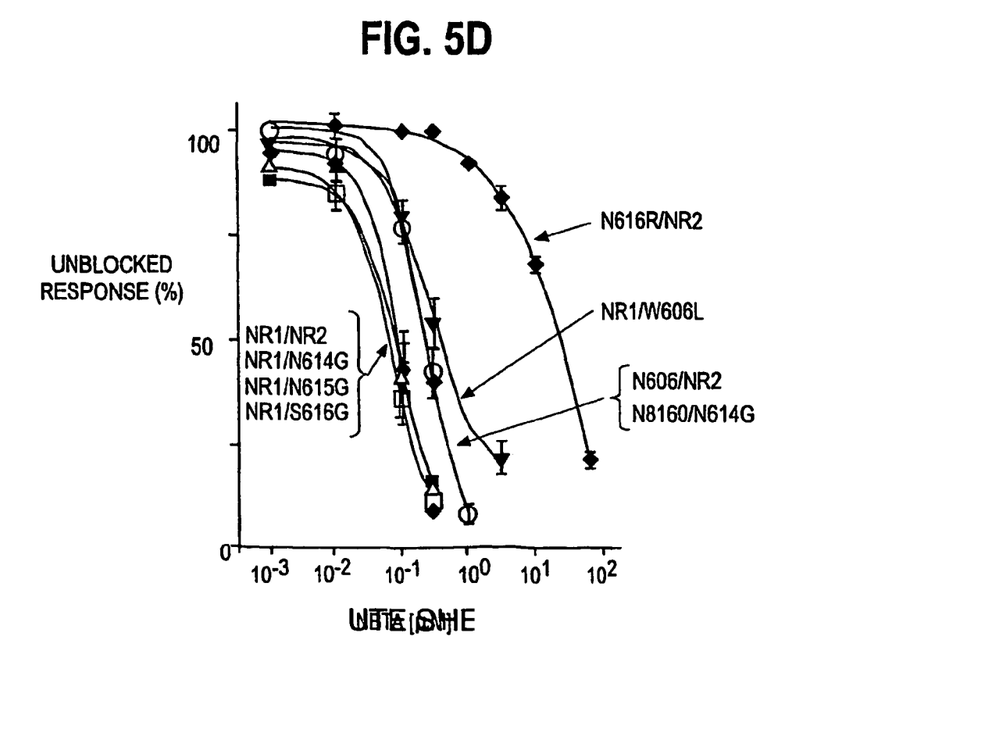

A critical asparagine, the N-site of NR1 subunit of NMDA receptors, is a structural determinant of ion permeation and channel blockade at the receptor pore. The N-site specifies the action of a wide array of open-channel blockers, including memantine, phencyclidine and MK-801 (Ferrer-Montiel A. V., et al., *Neuropharmacology*, 37(2):139–47, 1998), as well benzyl-polyamine derivatives. Examination was therefore made regarding whether NBTA binds to this critical asparagine (N-site). Substitution of the N-site to arginine (N616R) reduces the blocking activity of NBTA by 275 fold (FIG. 5D). In contrast, replacement of N616 for glutamine, which contains a similar functional group, only slightly reduces blocking activity (FIG. 5D), indicating that NBTA binds to the N-site of NR1.

A tryptophan to leucine substitution at the corresponding position of the NR2A subunit reduces the blocking activity of NBTA by 4.7 fold (FIG. 5D), suggesting that tryptophan 606 also contributes to the binding pocket for NBTA. In contrast, mutations at N614G, N615G and S616G in the M2 segment had no effect on NBTA binding. Furthermore, NBTA binding in the face of coexpression of N616Q (NR1 mutant) with N614G (NR2 mutant) was similar to binding achieved with N616Q alone, indicating that NBTA does not bind to asparagine 614 of NR2 (FIG. 5D). It is possible that the side-chains of the 614 and 615 asparagines of the NR2 subunit do not lie on the same level of the receptor as the NR1 N-site.

Figure 7:
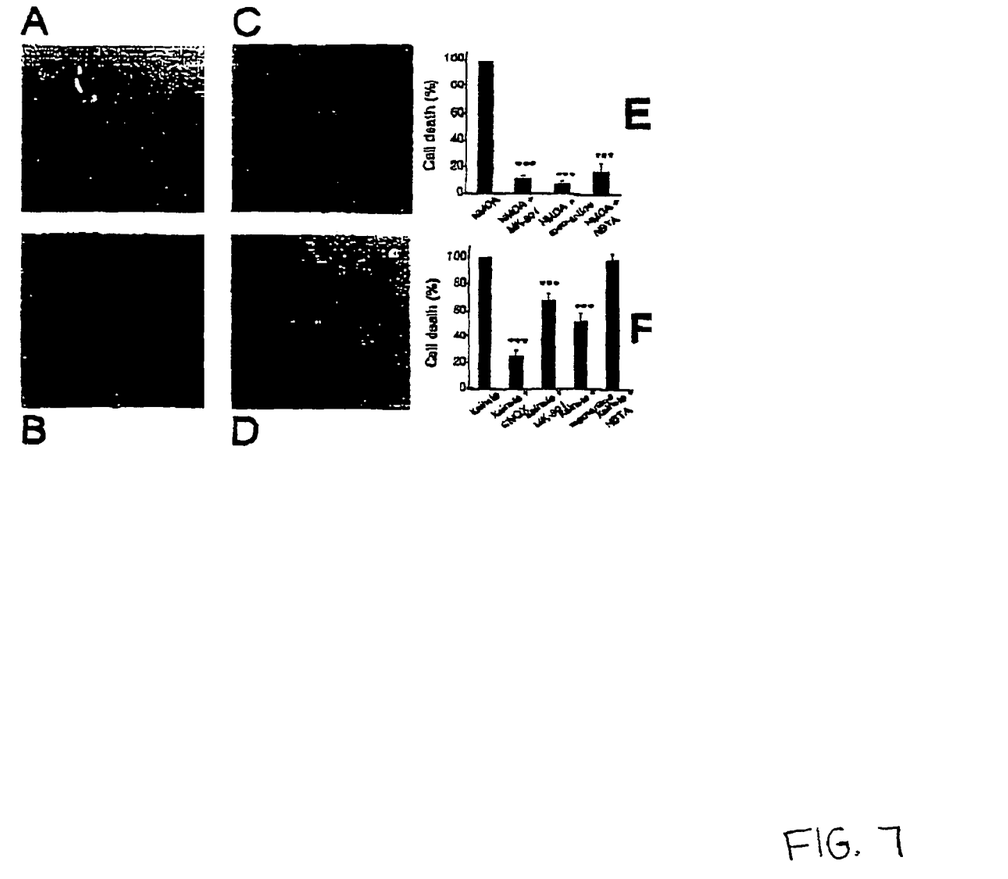
FIG. 7. NBTA protects cultured hippocampal neurons from NMDA receptor-mediated excitotoxic cell death. Trypan blue exclusion assays of (A) control neurons and neurons exposed to 200 μM NMDA in the absence (B) or presence of 10 μM memantine (C); and in the presence of 10 μM NBTA (D). (E) Normalized cell death in the absence and presence of the lead. (F) Neuronal death induced by kainate in the absence or presence of 20 μM CNQX, 10 μM MK-801, 10 μM memantine or 10 μM NBTA. Data are mean±s.e., n=2000.

D. NBTA Exerts a Neuroprotective Effect Against NMDA-Receptor Mediated Cell Death To determine whether NBTA has neuroprotective effect against NMDA-receptor mediated neurotoxicity, a model of excitotoxicity was employed. Cultured rat hippocampal neurons exposed to 200 µNMDA and 20 µM glycine for 20 min induced 50±3% of cell death (FIG. 7B). At 10 µM, NBTA protects hippocampal neurons from NMDA receptor-mediated cell death (83±2%) (FIG. 7D) to an extent comparable to that exerted by conventional NMDA blockers, such as memantine (93±1%) (FIGS. 7C and 6E) and MK-801 (89±1%) (FIG. 7E).

To evaluate the specificity of the neuroprotective effect of NBTA<its activity against kainate induced neuronal cell death was assessed. 6-cyano-7 nitroquinoxaline-2,3-dione (CNQX), an AMPA/kainate receptor antagonist, protects neurons from cell death induced by kainate (FIG. 7F). The NMDA blockers memantine and MK-801 protect neurons as well, though not as effectively as CNQX. In sharp contrast, NBTA has no effect on cell death mediated by the kainate receptor, demonstrating the specificity of NBTA for NMDA receptors (FIG. 5C).

The voltage-dependence of block produced by NBTA at the voltage-dependent site provides insight into the dimension of the NMDA receptor channel pore. It has been shown that both $Mg^{2+}$ and memantine has a δ of ~0.77 (21, 29, 30, 31, 32) and that the N-site located at the tip of M2 segment is their binding site. Because the N-site is not the binding site for NBTA, the vestibule of the receptors probably provides the binding site(s) for the compound. The blocking effect exhibited by this compound is characterized by a deep electrical depth (δ=0.56). The result implies that, unlike potassium channel pore where the majority of the transmembrane voltage (~80%) is imposed across the short selectivity filter (33, 34), a significant voltage drop occurs in the outer vestibule of the. NMDA channel pore.

The phenolic hydroxyl and the benzyl group define the structure-activity relationship of NBTA and are probably involved in interaction with amino residues in the outer vestibule of the channel. These two groups are separated apart by ~8.8 Å, implying that the outer vestibule of the NMDA pore right must be ~9 Å in order to accommodate the molecule. The size and configuration of NBTA therefore likely contribute to its greater potency as compared to the other inventive compounds described herein, although they also exert open channel blocking activity.

E. Pharmaceutical Compositions of NMDA Open Channel Blockers and Uses therefor

Any of the NMDA open channel blockers of the invention may be prepared in a pharmaceutically acceptable composition. Pharmaceutically acceptable carriers preferred for use in the invention may include sterile aqueous or non-aqueous solutions, suspensions, and emulsions.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. A composition of the invention may also be lyophilized using means well known in the art, for subsequent reconstitution and use in neuroprotection according to the invention.

Clinically, the neuroprotectants of the invention will be useful in the same therapies which are or may be practiced with known neuroprotectant agents which block NMDA receptor-mediated activity, with suitable adjustment for side effects and dosage (see, e.g., clinical reports regarding use of such agents as reported in Carter, A J, *J. Pharmacol. Exp. Ther.*, 269:573–580, 1994). Protocols for administering the neuroprotectants of the invention (including dosing schedules and concentrations) will depend on the patient's condition and the medical judgment of the clinician (see, use-dependence curve set forth in FIG. 5E). The concentration of neuroprotectants of the invention in a pharmaceutically acceptable carrier which produces a therapeutic benefit in a host is considered a "therapeutically effective dosage" of the neuroprotectant.

The invention having been fully described, examples illustrating its practice are provided below. These examples are non-limiting of the scope of the invention, whose scope will be defined by claims thereto.

Standard abbreviations used in the examples will be understood to have their common meaning ascribed in the art.

EXAMPLE I

Synthesis of the Library and Individual N-Alkylated Triamines

The N-alkylated triamine mixtures and individual compounds were synthesized on the solid phase using the "tea-bag" methodology (Houghten R. A., *Proc. Natl. Acad. Sci. USA*, 82:5131–5135, 1985) by selective alkylation and exhaustive reduction as described elsewhere (Dorner B., et al., *Bioorg. Medicinal Chem.*, 4:709–715, 1996; Ostresh J. M., et al., *J. Org. Chem.*, 63:8622–8623, 1998; Nefzi A., et al., *Tetrahedron*, 55:335–344, 1999). The mixtures were prepared using the divide, couple and recombine method (Houghten R. A., et al., *Nature*, 354(6348):84–6, 1991; Dorner B., et al., *Bioorg. Medicinal Chem.*, 4:709–715, 1996). In brief, the first amino acid was coupled using conventional Fmoc chemistry, and following removal of the Fmoc group, the N-terminal amino group was tritylated by reaction with a solution of trityl chloride (5 molar excess over the total free N-α-amino groups) for 3 hours at room temperature. N-alkylation was then performed by treatment of the resin packet with 1M lithium t-butoxide in tetrahydrofuran under a nitrogen atmosphere and strictly anhydrous conditions. Excess base was removed by cannulation, followed by addition of the individual alkylating agent in dimethylsulfoxide. The solution was vigorously shaken for 2 hours at room temperature. Upon removal of the trityl group with 2% trifluoroacetic acid in dichloromethane (2×10 min), the resin was washed, neutralized, and the second amino acid coupled and selectively alkylated as described above.

Exhaustive reduction was carried out in 50 ml kimax tubes under nitrogen (Ostresh J. M., et al., *J. Org. Chem.*, 63:8622–8623, 1998; Nefzi A., et al., *Tetrahedron*, 55:335–344, 1999) by addition of boric acid (40×) and trimethylborate (40×), followed by 1M borane in tetrahydrofuran (40×). The solutions were heated at 65° C. for 72 h, decanted, and quenched with methanol. Following overnight treatment with piperidine at 65° C., the mixtures or individual compounds were cleaved from the resin with anhydrous hydrogen fluoride, extracted, and lyophilized. The purity of the compounds was revealed by reverse phase high pressure liquid chromatography (HPLC) and the identity of each compound were confirmed by reverse phase HPLC and matrix assisted laser desorption ionization-mass spectroscopy (MALDI-MS). Results are as described in the Detailed Description of the Invention.

EXAMPLE II

Expression of NMDA Receptors in *Xenopus* Oocytes

Recombinant NMDA receptor subunits, NR1 (Planells-Cases R, et al., *Proc. Natl. Acad. Sci. USA*, 90(11):5057–61, 1993) and NR2A (Le Bourdelles B, et al., *J. Neurochem.*, 62(6):2091–8, 1994) was used for screening the dipeptidomimetic combinatorial library. cDNAs of NR1 and NR2A were linearized with NOT1. cRNAs encoding NR1 and NR2A were synthesized from the linearized cDNAs templates according to manufacturer specifications (Ambion). NR1 mutant (N616Q) was used to examine the site of action of the identified lead. The NR1A mutants were linearized with NOT1 and use of T7 for sense. cDNA of human glutamate receptor/GluR1 (Sun W., et al., *Proc. Natl. Acad. Sci. USA*, 89:1443–1447, 1992) was linearized with Hind III and the use of T3 promoter for the synthesis of its cDNA. cDNAs were quantified by spectroscopy and the quality were assessed by gel electrophoresis.

Oocytes of stage V and VI were surgically removed from the ovaries of Xenopus oocytes anesthetized with 0.4% ethyl 3-amino-benzoate methanesulfonic acid-Clusters of oocytes were incubated with 2 mg/ml collagenase (Life Technologies, Gaithersburg, Md.) for 1 hour 20 min in $Ca^{2+}$-free solution comprised of (mM) 82.5 NaCl, 2.5 KCl, 1 $MgCl_2$, 5 HEPES, pH 7.4 with vigorous agitation to remove the follicular cell layer. Oocytes were then washed extensively with the $Ca^{2+}$-free solution to remove the collagenase. Oocytes were eventually incubated in Barth's solution consisted of (in mM): 96 NaCl, 2 mM KCl, 1.8 $CaCl_2$, 1 $MgCl_2$, 5 HEPES supplemented with 100U/ml penicillin and 100 ug/ml streptomycin, pH 7.4 at 17° C. Oocytes were injected with 5–15 ng of cRNA encoding NR1 or its mutant premixed with three-fold amount of cRNA encoding NR2A.

Results are as described in the Detailed Description of the Invention.

EXAMPLE III

Electrophysiology of the NMDA Receptor

On days two to six following injection of cRNAs, whole oocyte currents were recorded with standard two-electrode voltage-clamp. All electrophysiological studies, unless otherwise stated, were performed in $Ba^{2+}$/flufenamic-Ringer's solution (in mM: 10 HEPES pH7.5, 115 NaCl, 2.8 KCl, 2.0 $BaCl_2$, 0.1 flufenamic, 0.1 niflumic acid) at ambient temperature as previously described (Ostresh J. M., et al., *J. Org. Chem.*, 63:8622–8623, 1998; Nefzi A., et al., *Tetrahedron*, 55:335–344, 1999). Both current and voltage electrodes were filled with 3M KCl and have a tested resistance of 0.5–1 MOhm. The blocking activities of the library were assessed at 10 µM (assuming the molecular weight is ~500). The screening of the subsequent twenty one compounds synthesized based on the primary screening were performed at 1 µM. Inward currents were elicited from a holding potential of −80 mV except where indicated. NMDA receptors were activated by abruptly exposing oocytes to 200 µM L-glutamic acid and 20 µM glycine followed by coperfusion with the library at indicated concentration. Blocking activity of the mixture is expressed as fraction of response blocked by the mixture. Dose-response curves were fitted to the Hill equation:

$$y = \frac{1}{1 + \left[\frac{[x]}{IC_{50}}\right]^{n_H}}$$

where y is the ratio of current in the presence and presence of blocker, [x] is the blocker concentration, and $IC_{50}$ and $n_H$ represent the concentration blocks 50% of response and Hill coefficient, respectively. Current-voltage relationships were measured first in the absence and then in the presence of a given concentration of lead at a specified membrane holding potential, and the ratio of these currents was plotted as a function of the holding potential. Analysis of the voltage dependent block current was performed according to the model proposed by Woodhull (Woodhull A. M., *J. Gen. Physiol.*, 61:687–708, 1973). Data were fitted with the equation according to Zarei and Dani (Zarei M. M. and Dani J. A., *J. Gen. Physiol.*, 1103(2):231–48, 1994):

$$\frac{I_b}{I_c} = \frac{1}{1 + \frac{[B]}{K_d \cdot e^{[z\delta \cdot F \cdot V/R \cdot T]}}}$$

where $I_b$ and $I_c$ are currents recorded during the blockade and control, respectively; [B] is the concentration of the blocker; $K_d$ is the dissociation constant of the blocker at 0 mV; δ is the fraction of the membrane field sensed by the blocker as it binds to its site; V is the command voltage; R is the gas constant; T is the absolute temperature; F is the Faraday's number; z is the valence of the blocker. Current signals were digitized and recorded using pClamp (version 6) software (Axon Instruments, Foster City, Calif.). Results are as described in the Detailed Description of the Invention.

EXAMPLE IV

Excitotoxic Assays in Hippocampal Cultures

Mixed hippocampal neuron/glia primary cultures were employed to assess the neuroprotective activities of the identified lead against NMDA receptor-mediated excitotoxic cell death. Primary culture of rat hippocampal neurons were prepared as previously described (Ferrer-Montiel A. V., et al., *Nat. Biotechnol.*, 16(3):286–91, 1998; Schinder A. F., et al.; *J. Neurosci.*, 16(19):6125–33, 1996). In brief, hippocampi from E17–E19 rat embryos were first taken out and incubated at 4° C. in a saline (BSS) containing (mM): 137 NaCl, 3.5 KCl, 0.4 $KH_2PO_4$, 0.33 $Na_2HPO_4.7H_2O$, 5 TES, and 10 glucose, pH 7.4. Hippocampi were then incubated in 0.25% trypsin (1×) solution from Hyclone at 37° C. for 15 min. Tissues were then washed and resuspended in minimal essential medium (Earle's salt) supplemented with 10% heat-inactivated horse serum (Hyclone), 10% fetal bovine serum (Hyclone), 1 mM glutamate, 22 mM glucose, 20U/ml penicillin and 20 ug/ml streptomycin. Digested hippocampi were eventually dissociated by pipetting through a Pasteur pipette. Cells were plated at a density of $5 \times 10^4$ cells/$cm^2$.

Neurons cultured 14–17 days were used for the excitotoxic assays. Cultured medium was first removed and rinsed with BSS supplemented with 1 mM $CaCl_2$, and 20 µM glycine. Neurons were challenged with 200 µM NMDA in the absence and presence of 10 the identified lead for 20 min at room temperature. The insults were terminated by removing the BSS containing NMDA. To reduce the excitotoxic effect due to the residual NMDA, the culture medium was supplemented with 20 µM MK-801. Cell cultures were returned to the incubator (37° C., 5% $CO_2$). Cell death was assessed 20–24 hours after the challenge with trypan blue (0.04%) exclusion assays. Fraction of dead cells in cultures treated with control buffer (8±3%, n=2000) was subtracted as background.

NMDA insult alone caused significant cell death of 45±6% (n=2000). Neuroprotective activities as described in the Detailed Description of the Invention were expressed as percentage of net cell death in the absence and presence of 10 µM of the known NMDA receptor blockers and the identified compound. Cell death elicited by NMDA alone was considered as 100%. The assays were repeated in 4 separated occasions with different culture preparations.

The invention claimed is:

1. A neuroprotectant agent selective for NMDA subtype glutamate receptors in the central nervous system, the agent comprising a compound having the formula:

wherein $R_1$ is S-4-hydroxylbenzyl or S-2-butyl; $R_2$ is benzyl; $R_3$ is selected from the group consisting of N-methyl, N-benzylaminobutyl, S-4-hydroxybenzyl (but not when $R_1$ is S-4-hydroxylbenzyl), R-2-naphthylmethyl, S-isopropyl, R-isobutyl and R-2-butyl; and $R_4$ is selected from the group consisting of benzyl, methyl, naphthylmethyl and ethyl.

2. The neuroprotectant agent according to claim 1, wherein $R_1$ is S-2-butyl, $R_2$ is benzyl, $R_3$ is S-4-hydroxybenzyl, and $R_4$ is benzyl.

3. A pharmaceutical composition, comprising the neuroprotectant agent of claim 1 and a pharmaceutically acceptable carrier therefor.

4. A pharmaceutical composition, comprising the neuroprotectant agent of claim 2 and a pharmaceutically acceptable carrier therefor.

5. A method for mitigating NMDA receptor excitoxicity in neuronal cells, the method comprising administering a therapeutically effective dosage of a neuroprotectant agent of claim 1 into the central nervous system of a host, wherein the neuroprotectant agent selectively exerts an open channel block on NMDA receptors in the host.

6. The method according to claim 5, wherein the neuroprotectant agent is the agent of claim 2.

* * * * *